(12) United States Patent
Handa et al.

(10) Patent No.: US 8,471,222 B2
(45) Date of Patent: Jun. 25, 2013

(54) RADIOTHERAPY APPARATUS CONTROL METHOD AND RADIOTHERAPY APPARATUS CONTROL APPARATUS

(75) Inventors: Takanobu Handa, Tokyo (JP); Shuji Kaneko, Tokyo (JP); Noritaka Yanai, Tokyo (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 501 days.

(21) Appl. No.: 12/808,312

(22) PCT Filed: Nov. 18, 2009

(86) PCT No.: PCT/JP2009/069587
§ 371 (c)(1),
(2), (4) Date: Aug. 27, 2010

(87) PCT Pub. No.: WO2011/061827
PCT Pub. Date: May 26, 2011

(65) Prior Publication Data
US 2011/0313228 A1    Dec. 22, 2011

(51) Int. Cl.
*A61N 5/10*    (2006.01)
*G21K 5/10*    (2006.01)
*G06T 7/20*    (2006.01)

(52) U.S. Cl.
CPC ............... *A61N 5/1069* (2013.01); *G21K 5/10* (2013.01)
USPC .............. 250/491.1; 378/20; 378/21; 378/64; 378/65; 382/128; 382/131; 382/132

(58) Field of Classification Search
CPC ..... A61N 5/10; G21K 5/00; G21K 5/10; G06T 7/20
USPC ...... 250/491.1; 378/20, 21, 64, 65; 382/128, 382/131, 132
See application file for complete search history.

(56) References Cited

U.S. PATENT DOCUMENTS 6,768,782 B1 * 7/2004 Hsieh et al. .................. 378/8
7,436,928 B2 * 10/2008 Urano et al. .................. 378/65

FOREIGN PATENT DOCUMENTS

| JP | 2001-259060 | 9/2001 |
|---|---|---|
| JP | 4159227 | 9/2001 |
| JP | 3825384 | 4/2004 |

(Continued)

OTHER PUBLICATIONS

Japanese Decision to Grant a Patent issued Apr. 6, 2012 in corresponding Japanese Patent Application No. 2010-512433 with English translation.

*Primary Examiner* — Jack Berman
(74) *Attorney, Agent, or Firm* — Wenderoth, Lind & Ponack, L.L.P.

(57) ABSTRACT

A radiotherapy apparatus control method according to the present invention includes: a step S6 of calculating rotational and first translational correction amounts based on a position and orientation of a first region represented by a radioscopic image of a subject; and a step S9 of calculating a second translational correction amount based on a position and orientation of the second region represented by the radioscopic image and the rotational correction amount; and a step S10 of driving a couch so that it rotates by the rotational correction amount and translates by the second translational correction amount. The first region is larger than the second region. According to such a method, the second region can be arranged in a predetermined position at higher accuracy compared with a case where the position of the couch is adjusted by using the position and orientation of only one of the first and second regions.

14 Claims, 4 Drawing Sheets

FOREIGN PATENT DOCUMENTS

| | | |
|---|---|---|
| JP | 2006-198119 | 8/2006 |
| JP | 2007-035020 | 2/2007 |
| JP | 4310319 | 9/2007 |
| WO | 2007/029520 | 3/2007 |

* cited by examiner

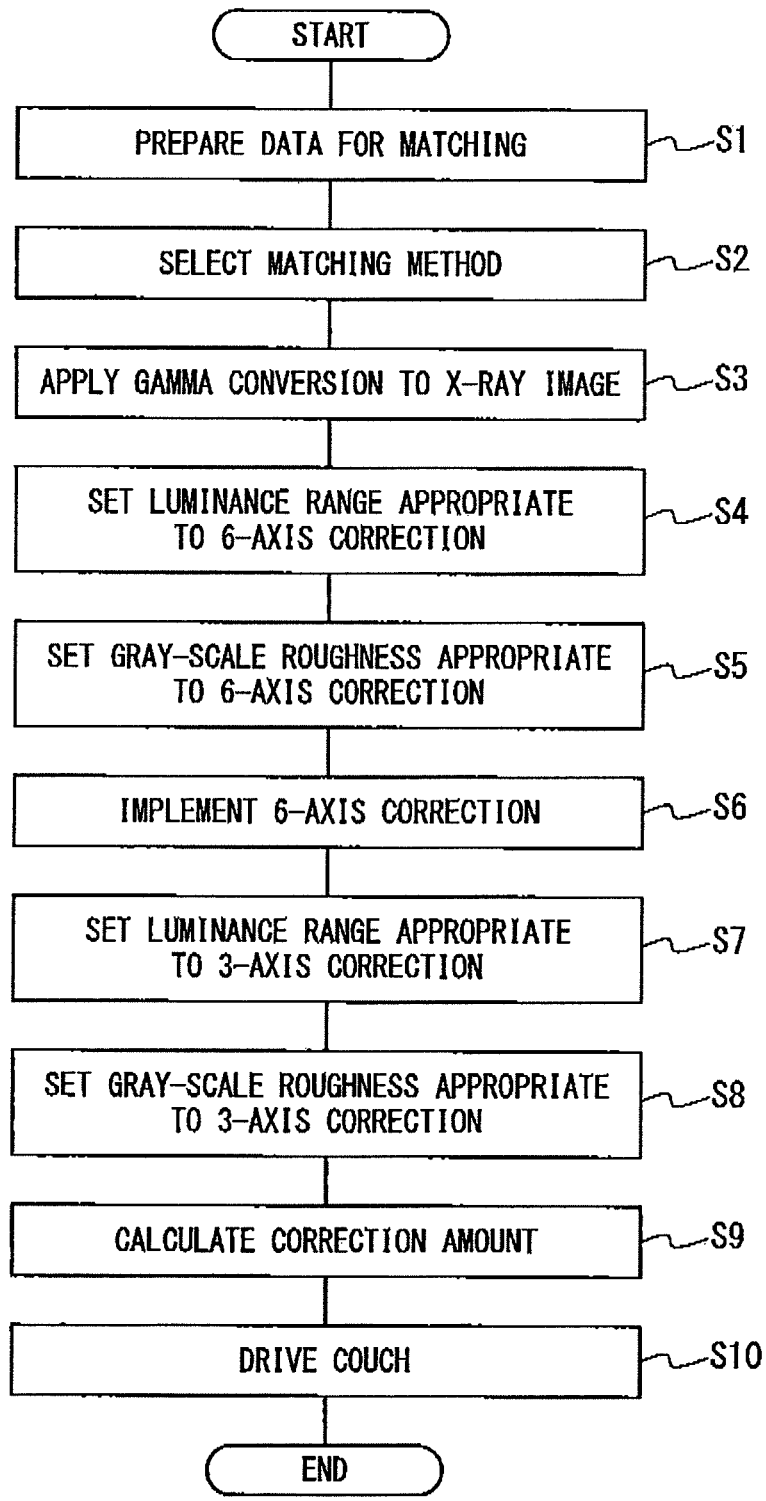

RADIOTHERAPY APPARATUS CONTROL METHOD AND RADIOTHERAPY APPARATUS CONTROL APPARATUS

TECHNICAL FIELD

The present invention relates to a radiotherapy apparatus control method and a radiotherapy apparatus control apparatus and, in particular, a radiotherapy apparatus control method and radiotherapy apparatus control apparatus for use in performing radiotherapy (including the particle-beam therapy) on an affected area of a tumor inside the human body.

BACKGROUND ART

The radiotherapy treatment is known in which a patient is treated with emission of a therapeutic radioactive ray for exposure onto an affected area of a tumor. A radiotherapy apparatus that performs the radiotherapy treatment includes a couch, an imager system that images an X-ray image of a patient laid on the couch, and a therapeutic radioactive-ray irradiating device that emits a therapeutic radioactive ray onto the patient. After the couch is positionally adjusted so that an affected area of the patient is arranged at a predetermined position based on a CT image of the patient shot previously and an X-ray image of the patient shot immediately before the radiotherapy treatment, the radiotherapy apparatus emits a therapeutic radioactive ray onto the affected area. In the radiotherapy treatment, it is desired to more accurately arrange the affected area of the patient at a predetermined position.

The Japanese Patent Publication No. 4159227 discloses a patient-position displacement measurement apparatus that improves positioning accuracy by directly measuring the position of an irradiation target in a soft-part tissue that is difficult to discriminate. As for the patient-position displacement measurement apparatus, a patient-position displacement measurement apparatus for measuring a displacement amount of a patient position from a target position includes storage means that stores all optical flows in which the motion of pixels on an image is represented by vectors within an expected range of a patient-position displacement amount previously calculated, measuring means that measures actual optical flows, and matching means that finds a position displacement amount of the patient by comparing a stored optical flow stored in the storage means and the measured optical flow actually measured.

The Japanese Patent Publication No. 3825384 discloses a radiotherapy apparatus that can easily position an irradiation target of a radioactive ray within a radioactive-ray irradiating range. The radiotherapy apparatus includes a radioactive-ray generating device that emits a radioactive ray and a laser light beam onto a same axis, at least three body surface markings indicating a position where the center axis of the radioactive ray is incident to a patient and having an azimuth set with respect to an irradiation target, a guide that arc-moves the radioactive-ray generating device about an isocenter along an orbit of a radius of a predetermined distance so that irradiation axes where the radioactive ray and the laser light beam are emitted onto the same axis cross at one point, a supporting member that rotate the guide about a tilt axis crosses a rotation axis of an arc-movement of the radioactive-ray generating device along the guide at the isocenter, a movable member that moves the radioactive-ray generating device along the guide, a slide board that moves the patient so that the body surface markings coincide with laser light beams projected from respective azimuths set by using the movable member, a detector that detects information of a radioscopic image in a range including the isocenter and the irradiation target of the radioactive ray arranged nearby, an analyzing device that computes a relative position relation between a position of the isocenter and a position of the irradiation target based on information about a plurality of the radioscopic images detected by the detector at the respective azimuths and information about the azimuths at which the radioscopic images are detected with respect to the isocenter, and a control device that causes the radioactive-ray generating device to move based on the relative position relation.

The Japanese Patent Publication No. 4310319 discloses a radiotherapy apparatus control apparatus that more accurately matches a predetermined position of a sample subject at a predetermined position of a radiotherapy apparatus. The radiotherapy apparatus control apparatus controls a radiotherapy apparatus that includes a therapeutic radioactive-ray irradiating device that irradiates a therapeutic radioactive ray, an imager that generates an imager image of the sample subject with a radioactive ray passing through the sample subject, and a driving device that moves a couch where the sample subject is arranged toward the therapeutic radioactive-ray irradiating device. The radiotherapy apparatus control apparatus includes a three-dimensional data generating part that generates a three-dimensional data of the sample subject based on a radioscopic image imaged by the imager, a two-dimensional image generating part that generates a two-dimensional image based on the three-dimensional data, a radioscopic-image imaging part that images an imaged imager image of the sample subject by using the imager, an affected-area position control part that determines, based on a position where a feature point included in the sample subject is reflected on the imaged imager image and a position where the feature point is reflected on the two-dimensional image, whether a relative position of the couch with respect to the therapeutic radioactive-ray irradiating device is appropriate, and a reference-image generating part that generates a reference imager image based on the imaged imager image, and the affected-area position control part further determines, based on a position where the feature point is reflected on another imaged imager image imaged by the imager and a position where the feature point is reflected on the reference imager image, whether the relative position of the couch with respect to the therapeutic radioactive-ray irradiating device is appropriate.

CITATION LIST

Patent Literature

Patent Literature 1: Japanese Patent Publication No. 4159227
Patent Literature 2: Japanese Patent Publication No. 3825384
Patent Literature 3; Japanese Patent Publication No. 4310319

SUMMARY OF INVENTION

A problem of the present invention is to provide a radiotherapy apparatus control method and radiotherapy apparatus control apparatus of more accurately adjusting the position of a patient.

Another problem of the present invention is to provide a radiotherapy apparatus control method and radiotherapy apparatus control apparatus of adjusting the position of a patient at higher speed.

A radiotherapy apparatus control method according to the present invention includes a step of calculating a rotational correction amount and a first translational correction amount based on a position and orientation of a first region represented by a radioscopic image of a sample subject having the first region and a second region and a step of calculating a second translational correction amount based on a position and orientation of the second region represented by the radioscopic image and the rotational correction amount. At this time, the rotational correction amount and the first translational correction amount are calculated so that the first region is arranged at a predetermined region when a couch where the sample subject is arranged makes a rotational movement by the rotational correction amount and the couch is translated by the first translational correction amount. The second translational correction amount is calculated so that the second region is arranged at a predetermined region when the couch where the sample subject is arranged makes a rotational movement by the rotational correction amount and the couch is translated by the second translational correction amount. The first region is larger than the second region.

According to the radiotherapy apparatus control method, compared with the case of adjusting the position of the couch by using only the position and orientation of the second region represented by the radioscopic image, the correction amount for rotatingly moving the couch can be more accurately calculated. According to the above-described radiotherapy apparatus control method, compared with the case of adjusting the position of the couch by using only the position and orientation of the first region represented by the radioscopic image, the correction amount for translating the couch can be more accurately calculated. As a result, according to the above-described radiotherapy apparatus control method, the couch can be positionally adjusted more accurately so that the second region is more accurately arranged at the predetermined position.

The radiotherapy apparatus control method according to the present invention further includes a step of collecting treatment plan three-dimensional data of the sample subject. At this time, the rotational correction amount and the first translational correction amount are calculated based on a first detection area matching a first template calculated based on the treatment plan three-dimensional data of the radioscopic image. The second translational correction amount is calculated based on a second detection area matching a second template calculated based on the treatment plan three-dimensional data of the radioscopic image and the rotational correction amount.

The first detection area is calculated with a feature point matching. The second detection area is calculated with a pattern matching different from the feature point matching. According to the above-described radiotherapy apparatus control method, the first detection area and the second detection area can be calculated each with an appropriate matching method and, as a result, the rotational correction amount and the second translational correction amount can be more accurately calculated, and the couch can be positionally adjusted more accurately so that the second region is more accurately arranged at the predetermined position.

The first detection area is calculated based on a first luminance-range-corrected radioscopic image converted from the radioscopic image. A range that can be taken by a plurality of luminances represented by the first luminance-range-corrected radioscopic image is narrower than a range that can be taken by the plurality of luminances represented by the radioscopic image. The second detection area is calculated based on a second luminance-range-corrected radioscopic image converted from the radioscopic image. A range that can be taken by a plurality of luminances represented by the second luminance-range-corrected radioscopic image is narrower than the range that can be taken by the plurality of luminances represented by the radioscopic image. According to the above-described radiotherapy apparatus control method, the amount of information when the first detection area and the second detection area are calculated can be decreased, the first detection area and the second detection area can be calculated at higher speed, and the couch can be positionally adjusted at higher speed.

The first detection area is calculated based on a gray-scale-roughness-corrected radioscopic image converted from the radioscopic image. A gray scale of the radioscopic image is finer than a gray scale of the gray-scale-roughness-corrected radioscopic image. According to the above-described radiotherapy apparatus control method, the amount of information when the first detection area and the second detection area are calculated can be decreased, the first detection area and the second detection area can be calculated at higher speed, and the couch can be positionally adjusted at higher speed.

The first detection area is calculated based on the gray-scale-corrected radioscopic image converted from. the radioscopic image so that a frequency distribution of a plurality of luminances represented by the gray-scale-corrected radioscopic image approximately coincides with a frequency distribution of a plurality of luminances represented by a DRR image calculated from the treatment plan three-dimensional data. The second detection area is calculated based on the gray-scale-corrected radioscopic image. According to the above-described radiotherapy apparatus control method, even when the treatment plan three dimensional data is created by a modality separate from an imager that images the radioscopic image, the second region can be more accurately arranged at the predetermined position.

A radiotherapy apparatus control apparatus according to the present invention includes an imager part that shoots a radioscopic image of a sample subject having a first region and a second region, a first correction part that calculates a rotational correction amount and a first translational correction amount based on a position and orientation of the first region represented by the radioscopic image, a second correction part that calculates a second translational correction amount based on a position and orientation of the second region represented by the radioscopic image and the rotational correction amount, and a couch control part that controls a couch driving device that drives the couch so that the couch where the sample subject is arranged rotationally moves by the rotational correction amount and the couch is translated by the second translational correction amount The first region is larger than the second region.

The radiotherapy apparatus control apparatus can more accurately calculate a correction amount for rotationally moving the couch, compared with the case of adjusting the position of the couch by using only the position and orientation of the second region represented by the radioscopic image. The above-described radiotherapy apparatus control apparatus can more accurately calculate a correction amount for translating the couch, compared with the case of adjusting the position of the couch by using only the position and orientation of the first region represented by the radioscopic image. As a result, the above-described radiotherapy apparatus control apparatus can more accurately arrange the second region at a predetermined position.

The radiotherapy apparatus control apparatus according to the present invention further includes a treatment plan collection part that collects treatment plan three-dimensional data of the sample subject. The first correction part calculates the rotational correction amount and the first translational correction amount based on a first detection area matching a first template calculated based on the treatment plan three-dimensional data of the radioscopic image. The second correction part calculates the second translational correction amount based on a second detection area matching a second template calculated based on the treatment plan three-dimensional data of the radioscopic image and the rotational correction amount.

The first correction part calculates the first detection area with a feature point matching. The second correction part calculates the second detection area with a pattern matching different from the feature point matching. The above-described radiotherapy apparatus control apparatus can calculate the first detection area and the second detection area each with an appropriate matching method and, as a result, the rotational correction amount and the second translational correction amount can be more accurately calculated, and the couch can be positionally adjusted more accurately so that the second region is more accurately arranged at the predetermined position.

The first correction part calculates the first detection area based on a first luminance-range-corrected radioscopic image converted from the radioscopic image. The range that can be taken by a plurality of luminance represented by the first luminance-range-corrected radioscopic image is narrower than a range that can be taken by the plurality of luminances represented by the radioscopic image, and the second correction part calculates the second detection area based on a second luminance-range-corrected radioscopic image converted from the radioscopic image. A range that can be taken by a plurality of luminances represented by the second luminance-range-corrected radioscopic image is narrower than the range that can be taken by the plurality of luminances represented by the radioscopic image. In the above-described radiotherapy apparatus control apparatus, the amount of information when the first detection area and the second detection area are calculated can be decreased, the first detection area and the second detection area can be calculated at higher speed, and the couch can be positionally adjusted at higher speed.

The first correction part calculates the first detection area based on a gray-scale-roughness-corrected radioscopic image converted from the radioscopic image. A gray scale of the radioscopic image is finer than a gray scale of the gray-scale-roughness-corrected radioscopic image. In the above-described radiotherapy apparatus control apparatus, the amount of information when the first detection area and the second detection area are calculated can be decreased, the first detection area and the second detection area can be calculated at higher speed, and the couch can be positionally adjusted at higher speed.

The first correction part calculates the first detection area based on the gray-scale-corrected radioscopic image converted from the radioscopic image so that a frequency distribution of a plurality of luminances represented by the gray-scale-corrected radioscopic image approximately coincides with a frequency distribution of a plurality of luminances represented by a DRR image calculated from the treatment plan three-dimensional data. The second correction part calculates the second detection area based on the gray-scale-corrected radioscopic image. In the above-described radiotherapy apparatus control apparatus, even when the treatment plan three dimensional data is created by a modality separate from an imager that images the radioscopic image, the second region can be more accurately arranged at the predetermined position.

The radiotherapy apparatus control apparatus according to the present invention further includes an irradiation part that controls the therapeutic radioactive-ray irradiating device so that the therapeutic radioactive ray is emitted for exposure onto the second region. In the above-described radiotherapy apparatus control apparatus, by more accurately arranging the second region at a predetermined position, the therapeutic radioactive ray can be more accurately emitted for exposure onto the second region.

The irradiation part controls, based on the other radioscopic image, a swing device that drives a treatment radioactive-ray irradiating device so that, after the imager that shot the radioscopic image is used to shoot another radioscopic image of the sample subject, the treatment radioactive ray is emitted for exposure onto the second region. The above-described radiotherapy apparatus control apparatus is suitable for tracking and irradiating a moving subject with the treatment radioactive ray.

The radiotherapy apparatus control method and radiotherapy apparatus control apparatus according to the present invention can more accurately adjust the position of a patient.

BRIEF DESCRIPTION OF DRAWINGS

FIG. 6 is a flowchart of an operation of adjusting the position of a patient.

DESCRIPTION OF EMBODIMENTS

Figure 1:
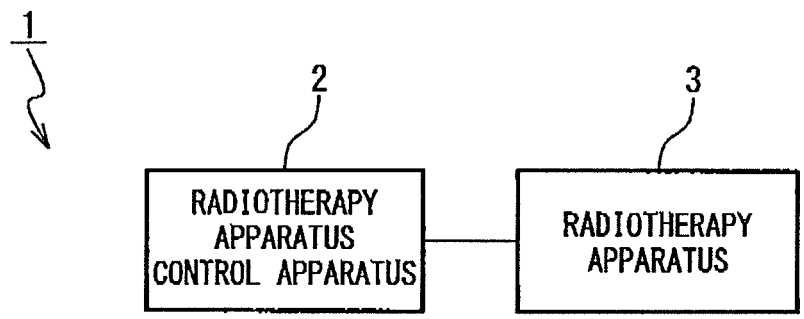
FIG. 1 is a block diagram of a radiotherapy system.

Referring to the drawings, embodiments of a radiotherapy apparatus control apparatus according to the present invention are described. As depicted in FIG. 1, a radiotherapy apparatus control apparatus 2 is applied to a radiotherapy system 1. The radiotherapy system 1 includes the radiotherapy apparatus control apparatus 2 and a radiotherapy apparatus 3. The radiotherapy apparatus control apparatus 2 is a computer exemplified by a personal computer. The radiotherapy apparatus control apparatus 2 and the radiotherapy apparatus 3 are connected to each other so that they can bidirectionally transmit information to each other.

Figure 2:
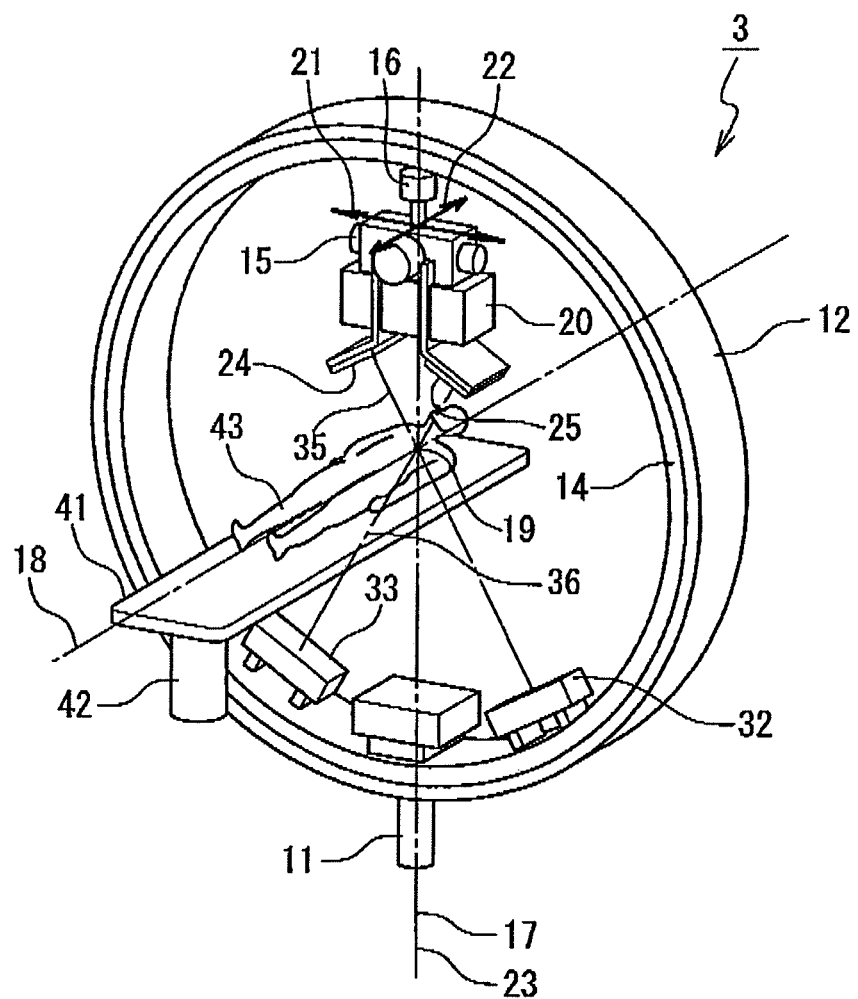
FIG. 2 is a perspective view of a radiotherapy apparatus.

FIG. 2 depicts the radiotherapy apparatus 3. The radiotherapy apparatus 3 includes an O ring 12, a traveling gantry 14, and a therapeutic radioactive-ray irradiating device 16. The O ring 12 is formed in a ring shape, and is supported by a base so as to be able to rotate about a rotation axis 17. The rotation axis 17 is parallel to the vertical direction. The traveling gantry 14 is formed in a ring shape, is arranged on the inside surface of the O ring 12, and is supported by the O ring 12 so as to be able to rotate about a rotation axis 18. The rotation axis 18 is perpendicular to a vertical direction, and passes through the isocenter 19 included in the rotation axis 17. The rotation axis 18 is fixed with respect to the O ring 10 12, that is, rotates about the rotation axis 17 with the O ring 12.

The therapeutic radioactive-ray irradiating device 16 is arranged inside a ring of the traveling gantry 14. The therapeutic radioactive-ray irradiating device 16 is supported by the traveling gantry 14 so as to be able to rotate around a tilt axis 21 and a pan axis 22. The pan axis 22 is fixed to the traveling gantry 14, and is parallel to a rotation axis 18 without crossing the rotation axis 18. The tilt axis 21 is orthogonal to the pan axis 22. A point of intersection of the tilt axis 21 and the pan axis 22 is 1 meter away from the isocenter 19.

The radiotherapy apparatus 3 further includes a rotary driving device 11 and a swinging device 15, and also includes a traveling driving device not shown. The rotary driving device 11 rotates the O ring 12 about the rotation axis 17 in accordance with the control by the radiotherapy apparatus control apparatus 2. The rotary driving device 11 further measures a rotary angle at which the O ring 12 is arranged on the base, and outputs the rotary angle to the radiotherapy apparatus control apparatus 2. The traveling driving device rotates the traveling gantry 14 about the rotation axis 18 in accordance with the control by the radiotherapy apparatus control apparatus 2. The traveling driving device further measures a gantry angle at which the traveling gantry 14 is arranged on the O ring 12, and outputs the gantry angle to the radiotherapy apparatus control apparatus 2. The swinging device 15 rotates the therapeutic radioactive-ray irradiating device 16 about the pan axis 22, and rotates the therapeutic radioactive-ray irradiating device 16 about the tilt axis 21 in accordance with the control by the radiotherapy apparatus control apparatus 2.

The therapeutic radioactive-ray irradiating device 16 emits a therapeutic radioactive ray 23 for exposure in accordance with the control by the radiotherapy apparatus control apparatus 2. The therapeutic radioactive ray 23 is a cone beam with the point of intersection of the pan axis 22 and the tilt axis 21 being taken as a vertex. The therapeutic radioactive ray 23 is formed so as to have a uniform intensity distribution. The therapeutic radioactive-ray irradiating device 16 includes a multi-leaf collimator 20. The multi-leaf collimator 20 is fixed to the therapeutic radioactive-ray irradiating device 16 so as to be arranged in an area where the therapeutic radioactive ray 23 proceeds. The multi-leaf collimator 20 shields part of the therapeutic radioactive ray 23 and changes the shape of an irradiation field when a patient is irradiated with the therapeutic radioactive ray 23 in accordance with the control by the radiotherapy apparatus control apparatus 2.

With the therapeutic radioactive-ray irradiating device 16 being supported by the traveling gantry 14, the therapeutic radioactive-ray irradiating device 16 is fixed to the traveling gantry 14 so as to be oriented to the isocenter 19. With this, when the O ring 12 is rotated by the rotary driving device 11 or the traveling gantry 14 is rotated by the traveling driving device, the therapeutic radioactive ray 23 always passes approximately through the isocenter 19. That is, with traveling and rotation, irradiation of the therapeutic radioactive ray 23 toward the isocenter 19 from any direction can be made.

The radiotherapy apparatus 3 further includes a plurality of imager systems. That is, the radiotherapy apparatus 3 includes a first diagnostic X-ray source 24, a second diagnostic X-ray source 25, a first sensor array 32, and a second sensor array 33. The first diagnostic X-ray source 24 is supported by the traveling gantry 14, and is arranged inside the ring of the traveling gantry 14 so that the angle formed by the line connecting the isocenter 19 to the first diagnostic X-ray source 24 and the line connecting the isocenter 19 to the therapeutic radioactive-ray irradiating device 16 has an acute angle. The second diagnostic X-ray source 25 is supported by the traveling gantry 14, and is arranged inside the ring of the traveling gantry 14 so that the angle formed by the line connecting the isocenter 19 to the second diagnostic X-ray source 25 and the line connecting the isocenter 19 to the therapeutic radioactive-ray irradiating device 16 has an acute angle. The second diagnostic X-ray source 25 is further arranged so that the angle formed by the line isocenter 19 to the first diagnostic X-ray source 24 and the line connecting the isocenter 19 to the second diagnostic X-ray source 25 has the right angle (90 degrees). The first sensor array 32 is supported by the traveling gantry 14, and is arranged so as to face the first diagnostic X-ray source 24 via the isocenter 19. The second sensor array 33 is supported by the traveling gantry 14, and is arranged so as to face the second diagnostic X-ray source 25 via the isocenter 19.

The first diagnostic X-ray source 24 emits a first diagnostic X-ray 35 for exposure toward the isocenter 19 at a predetermined timing in accordance with the control by the radiotherapy apparatus control apparatus 2. The first diagnostic X-ray 35 is a corn beam in a conical shape emitted for exposure from one point of the first diagnostic X-ray source 24 and having that point as a vertex. The second diagnostic X-ray source 25 emits a second diagnostic X-ray 36 for exposure toward the isocenter 19 at a predetermined timing in accordance with the control by the radiotherapy apparatus control apparatus 2. The second diagnostic X-ray 36 is a corn beam in a conical shape emitted for exposure from one point of the second diagnostic X-ray source 25 and having that point as a vertex.

The first sensor array 32 includes a light-receiving part. The first sensor array 32 generates a first X-ray image based on an X-ray received by the light-receiving part in accordance with the control by the radiotherapy apparatus control apparatus 2. The second sensor array 33 includes a light-receiving part. The second sensor array 33 generates a second X-ray image based on an X-ray received by the light-receiving part in accordance with the control by the radiotherapy apparatus control apparatus 2. The X-ray image is formed of a plurality of pixels. The plurality of pixels are arranged in a matrix on the X-ray image, and are each associated with a luminance. With the luminance corresponding to each of the plurality of pixels being colored onto each of the plurality of pixels, the X-ray image reflects a subject. As an example of the first sensor array 32 and the second sensor array 33, the FPD (Flat Panel Detector) and the X-ray II (Image Intensifier) can be exemplified.

According to such an imager system, based on image signals obtained from the first sensor array 32 and the second sensor array 33, an X-ray image centering on the isocenter 19 can be generated.

The radiotherapy apparatus 3 further includes a couch 41 and a couch driving device 42. The couch 41 is supported by a base so as to be able to make a rotational movement about an x axis, a y axis, and a z axis, and so as to be able to make a translational movement in parallel to the x axis, the y axis, and the z axis. The x axis, the y axis, and the z axis are perpendicular to each other. The couch 41 is used for laying a patient 43 to be treated by the radiotherapy system 1. The couch 41 includes a fixation device not shown. The fixation device fixes the patient 43 to the couch 41 so that the patient 43 does not move. The couch driving device 42 causes the couch 41 to make rotational and translational movements in accordance with the control by the radiotherapy apparatus control apparatus 2.

Figure 3:
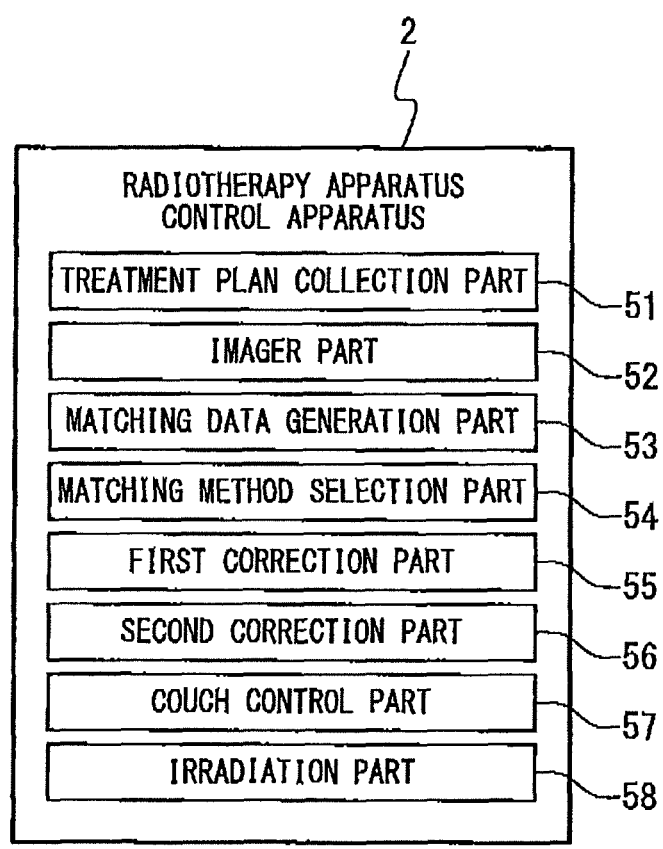
FIG. 3 is a block diagram of a radiotherapy apparatus control apparatus.

FIG. 3 depicts the radiotherapy apparatus control apparatus 2. The radiotherapy apparatus control apparatus 2 is a computer, includes a CPU, a storage device, a removable memory drive, a communication device, an input device, an output device, and an interface not shown. The CPU executes a computer program installed on the radiotherapy apparatus control apparatus 2 to control the storage device, the input device, and the output device. The storage device records the computer program, records information for use in the CPU, and records information generated by the CPU. The removable memory drive is used for reading data recorded in a recording medium when a recording medium is inserted. In particular, the removable memory drive is used, when a recording medium having recorded therein a computer program is inserted, for installing the computer program on the radiotherapy apparatus control apparatus 2. The communication device downloads information distributed from another computer connected via a communication line network to the radiotherapy apparatus control apparatus 2. In particular, the communication device is used for downloading a computer program from another computer to the radiotherapy apparatus control apparatus 2 and installing the computer program on the radiotherapy apparatus control apparatus 2. The input device outputs, to the CPU, information generated by a user operating the input device. The input device is exemplified by a keyboard and a mouse. The output device outputs information generated by the CPU to the user in a recognizable manner. The output device is exemplified by a display that displays an image generated by the CPU.

The interface outputs information generated by external devices connected to the radiotherapy apparatus control apparatus 2 to the CPU, and outputs information generated by the CPU to the external devices. The external devices include the rotary driving device 11, the traveling driving device, the swinging device 15, the therapeutic radioactive-ray irradiating device 16, the multi-leaf collimator 20, the first diagnostic X-ray source 24, the second diagnostic X-ray source 25, the first sensor array 32, the second sensor array 33 and the couch driving device 42 of the radiotherapy apparatus 3.

The computer program to be installed on the radiotherapy apparatus control apparatus 2 is formed of a plurality of computer programs for causing the radiotherapy apparatus control apparatus 2 to achieve each of a plurality of functions. The plurality of functions include a treatment plan collection part 51, an imager part 52, a matching data generation part 53, a matching method selecting part 54, a first correction part 55, a second correction part 56, a couch control part 57, and an irradiation part 58.

The treatment plan collection part 51 collects a treatment plan from the input device. The treatment plan represents three-dimensional data, and represents the combination of the irradiation angle and the dose. The three-dimensional data associates a plurality of transmittances with a plurality of voxels. The plurality of voxels correspond to a plurality of rectangular cuboids tightly filling a space where the patient 43 is arranged. Each rectangular cuboid is exemplified by a cube with its one side having a length of 0.4 mm. The transmittance corresponding to each voxel represents an X-ray transmittance of a cube at a position corresponding to the voxel. The three-dimensional data represents stereoscopic shapes of a plurality of organs of the patient 43 laid on the bed and a plurality of positions where the plurality of organs are respectively arranged. The irradiation angle represents the direction in which an affected area of the patient 43 is irradiated with the therapeutic radioactive ray 23, and represents the couch position, the O-ring rotation angle, and the gantry rotation angle. The couch position represents the position of the couch 41 with respect to the base. The O-ring rotation angle represents the position of the O ring 12 with respect to the base. The gantry rotation angle represents the position of the traveling gantry 14 with respect to the O ring 12. The dose represents a dose of the therapeutic radioactive ray 23 with which the patient 43 is irradiated at each irradiation angle.

The imager part 52 controls the radiotherapy apparatus 3 so that two X-ray images reflecting the patient 43 laid on the couch 41 are shot. That is, the imager part 52 controls the couch driving device 42 so that the couch 41 is arranged at a predetermined position with respect to the base. The imager part 52 controls the rotary driving device 11 so that the O ring 12 is arranged at a predetermined rotary angle with respect to the base. The imager part 52 further controls the traveling driving device of the radiotherapy apparatus 3 so that the traveling gantry 14 is arranged at a predetermined traveling angle. The imager part 52 further controls the first diagnostic X-ray source 24 so that the first diagnostic X-ray 35 is emitted for exposure. The imager part 52 further controls the first sensor array 32 so that a first X-ray image is generated when the first diagnostic X-ray 35 is emitted for exposure. The imager part 52 further controls the second diagnostic X-ray source 25 so that the second diagnostic X-ray 36 is emitted for exposure. The imager part 52 further controls the second sensor array 33 so that a second X-ray image is generated when the second diagnostic X-ray 36 is emitted for exposure.

The matching data generation part 53 generates a first DRR image and a second DRR image based on three-dimensional data of a treatment plan collected by the treatment plan collection part 51. The first DRR image represents an image assumed to be generated by the first sensor array 32 when the patient 43 represented by the three-dimensional data is laid on the couch 41. The second DRR image represents a second x-ray image assumed to be generated by the second sensor array 33 when the patient 43 represented by the three-dimensional data is laid on the couch 41.

The matching method selection part 54 calculates a first matching method and a second matching method based on information inputted via the input device. The first matching method represents one method of calculating a position and orientation where a predetermined image is displayed on the first X-ray image or the second X-ray image, and is either one of, for example, "a pattern matching" and "a feature point matching". The second matching method represents one method of calculating a position and orientation where a predetermined image is displayed on the first X-ray image or the second X-ray image, and is either one of, for example, "a pattern matching" and "a feature point matching".

The first correction part 55 corrects the first X-ray image generated by the imager part 52 to a gamma-corrected first X-ray image. The gamma-corrected first X-ray image is calculated so that the frequency distribution of a plurality of luminances represented by the gamma-corrected first X-ray image approximately coincides with the frequency distribution of a plurality of luminances represented by the first DRR image calculated by the matching data generation part 53. That is, the gamma-corrected first X-ray image is gamma-converted so that a gamma characteristic of the gamma-corrected first X-ray image coincides with a gamma characteristic of the first DRR image.

The first correction part 55 further corrects the gamma-corrected first X-ray image to a luminance-range-corrected first X-ray image. The luminance-range-corrected first X-ray image is formed of pixels included within a predetermined luminance range among the plurality of pixels constructing the gamma-corrected first X-ray image. The luminance range represents the range of values that can be taken by the plurality of luminances respectively represented by the plurality of pixels constructing an image reflecting a first region (bones) on the first DRR image.

The first correction part 55 further corrects the luminance-range-corrected first X-ray image to a gray-scale-roughness-corrected first X-ray image. The gray-scale-roughness-corrected first X-ray image is calculated so that the number of values (the number of gray-scale levels) that can be taken by the plurality of luminances represented by the plurality of pixels constructing the gray-scale-roughness-corrected first X-ray image is smaller than the number of values (the number of gray-scale levels) that can be taken by the plurality of luminances represented by the plurality of pixels constructing the luminance-range-corrected first X-ray image. The number of gray-scale levels of the gray-scale-roughness-corrected first X-ray image is calculated so that an image reflecting the first region (bones) can be sufficiently extracted from the gray-scale-roughness-corrected first X-ray image.

The first correction part 55 further uses a first matching method selected from the matching method selection part 54 to calculate the position and orientation of the image of the first region reflected on the gray-scale-roughness-corrected first X-ray image.

The first correction part 55 further calculates, for the second X-ray image generated by the imager part 52, a gamma-corrected second X-ray image, a luminance-range-corrected second X-ray image, and a gray-scale-roughness-corrected second X-ray image, in a manner similar to that for the first X-ray image. The first correction part 55 further uses a first matching method selected by the matching method selection part 54 to calculate a position and orientation of the image of the first region reflected on the gray-scale-roughness-corrected second X-ray image.

The first correction part 55 further calculates a rotational correction amount and a translational correction amount based on the position and orientation of the image of the first region reflected on the gray-scale-roughness-corrected first X-ray image and the position and orientation of the image of the first region reflected on the gray-scale-roughness-corrected second X-ray image. The rotational correction amount is formed of an x-axis rotational correction amount, a y-axis rotational correction amount, and a z-axis rotational correction amount. The x-axis rotational correction amount represents a rotation angle at which the couch 41 is rotated about the x axis. The y-axis rotational correction amount represents a rotation angle at which the couch 41 is rotated about the y axis. The z-axis rotational correction amount represents a rotation angle at which the couch 41 is rotated about the z axis. The translational correction amount represents a distance and orientation in which the couch 41 is translated, and is formed of an x-axis translational correction amount, a y-axis translational correction amount, and a z-axis translational correction amount. The x-axis translational correction amount represents a distance in which the couch 41 is translated in parallel to an x axis. The y-axis translational correction amount represents a distance in which the couch 41 is translated in parallel to a y axis. The z-axis translational correction amount represents a distance in which the couch 41 is translated in parallel to a z axis. The rotational correction amount and the translational correction amount are calculated so that the first region of the patient 43 arranged on the couch 41 is arranged at a predetermined position when the couch 41 is rotated about the x axis by the x-axis rotational correction amount, the couch 41 is rotated about the y axis by the y-axis rotational correction amount after the couch 41 is rotated about the x axis, the couch 41 is rotated about the z axis by the z-axis rotational correction amount after the couch 41 is rotated about the y axis, and the couch 41 is translated by the translational correction amount after the couch 41 is rotated about the z axis. The predetermined position represents the position of the first region represented by three-dimensional data of the treatment plan collected by the treatment plan collection part 51.

The second correction part 56 corrects the first X-ray image generated by the imager part 52 to a gamma-corrected first X-ray image. The gamma-corrected first X-ray image is calculated so that a frequency distribution of a plurality of luminances represented by the gamma-corrected first X-ray image approximately coincides with a frequency distribution of a plurality of luminances represented by the first DRR image calculated by the matching data generation part 53.

That is, the gamma-corrected first X-ray image is gamma-converted so that the gamma characteristic of the gamma-corrected first X-ray image coincides with the gamma characteristic of the first DRR image. That is, the gamma-corrected first X-ray image coincides with the gamma-corrected first X-ray image calculated by the first correction part 55, and the gamma-corrected first X-ray image calculated by the first correction part 55 can be used.

The second correction part 56 further corrects the gamma-corrected first X-ray image to a luminance-range-corrected first X-ray image. The luminance-range-corrected first X-ray image is formed of pixels included within a predetermined luminance range among the plurality of pixels constructing the gamma-corrected first X-ray image. The luminance range represents a range of values that can be taken by the plurality of luminances respectively represented by the plurality of pixels constructing an image reflecting a second region (affected area) on the first DRR image. The luminance range is smaller than a luminance range applied when a luminance-range-corrected first X-ray image is calculated by the first correction part 55.

The second correction part 56 further corrects the luminance-range-corrected first X-ray image to a gray-scale-roughness-corrected first X-ray image. The gray-scale-roughness-corrected first X-ray image is calculated so that the number of values (the number of gray-scale levels) that can be taken by the plurality of luminances represented by the plurality of pixels constructing the gray-scale-roughness-corrected first X-ray image is smaller than the number of values (the number of gray-scale levels) that can be taken by the plurality of luminances represented by the plurality of pixels constructing the luminance-range-corrected first X-ray image. The number of gray-scale levels of the gray-scale-roughness-corrected first X-ray image is calculated so that an image reflecting the second region (affected area) can be sufficiently extracted from the gray-scale-roughness-corrected first X-ray image and so that the number of gray-scale levels is greater than the number of gray-scale levels applied when a gray-scale-roughness-corrected first X-ray image is calculated by the first correction part 55.

The second correction part 56 further uses a second matching method selected from the matching method selection part 54 to calculate the position and orientation of the image of the second region reflected on the gray-scale-roughness-corrected first X-ray image.

The second correction part 56 further calculates, for the second X-ray image generated by the imager part 52, a gamma-corrected second X-ray image, a luminance-range-corrected second X-ray image, and a gray-scale-roughness-corrected second X-ray image, in a manner similar to those for the first X-ray image. The second correction part 56 further uses a second matching method selected by the matching method selection part 54 to calculate the position and orientation of the image of the second region reflected on the gray-scale-roughness-corrected second X-ray image.

Note that the second correction part 56 can use an initial value calculated based on the translational correction amount calculated by the first correction part 55 to calculate the position and orientation of the second region reflected on the gray-scale-roughness-corrected first X-ray image or the gray-scale-roughness-corrected second X-ray image at higher speed. At this time, the second correction part 56, compared with the case of calculating the position and orientation of the image of the second region without using the initial value, the position and orientation of the image of the second region can be calculated at higher speed.

The second correction part 56 further calculates a translational correction amount based on the rotational correction amount calculated by the first correction part 55, and further based on the position and orientation of the image of the second area reflected on the gray-scale-corrected first X-ray image and the position and orientation of the image of the second region reflected on the gray-scale-roughness-corrected second x-ray. The translational correction amount represents a distance and orientation in which the couch 41 is translated, and is formed of an x-axis translational correction amount, a y-axis translational correction amount, and a z-axis translational correction amount. The x-axis translational correction amount represents a distance in which the couch 41 is translated in parallel to an x axis. The y-axis translational correction amount represents a distance in which the couch 41 is translated in parallel to a y axis. The z-axis translational correction amount represents a distance in which the couch 41 is translated in parallel to a z axis. The rotational correction amount is calculated so that the second region of the patient 43 arranged on the couch 41 is arranged at a predetermined position when the couch 41 rotates by an amount represented by the rotational correction amount and then is translated by the translational correction amount. The predetermined position represents the position of the second region represented by three-dimensional data of the treatment plan collected by the treatment plan collection part 51.

The couch control part 57 controls the couch driving device 42 based on the rotational correction amount calculated by the first correction part 55 and the translational correction amount calculated by the second correction part 56. That is, the couch control part 57 controls the couch driving device 42 so that the couch 41 rotates about the x axis by the x-axis rotational correction amount, the couch 41 rotates about the y axis by the y-axis rotational correction amount after the couch 41 rotates about the x axis, the couch 41 rotates about the z axis by the z-axis rotational correction amount after the couch 41 rotates about the y axis, and the couch 41 is translated by the translational correction amount after the couch 41 rotates about the z axis.

The irradiation part 58 controls the radiotherapy apparatus 3 so that radiotherapy indicated by the treatment plan collected by the treatment plan collection part 51 is performed. That is, the irradiation part 58 controls the couch driving device 42, controls the rotary driving device 11, and controls the traveling driving device of the radiotherapy apparatus 3 so that the therapeutic radioactive-ray irradiating device 16 is arranged with respect to the patient 43 at an irradiation angle indicated by the treatment plan. The irradiation part 58 further controls the first diagnostic X-ray source 24, the second diagnostic X-ray source 25, the first sensor array 32, and the second sensor array 33 so that two X-ray images of the patient 43 are shot. The irradiation part 58 further calculates the position of the affected area of the patient 43 based on these two X-ray images to calculate the shape of the affected area. The irradiation part 58 further controls the swinging device 15 so that the therapeutic radioactive-ray irradiating device 16 is oriented to the calculated position of the affected area. The irradiation part 58 further controls the multi-leaf collimator 20 so that the shape of the affected area coincides with the irradiation field of the therapeutic radioactive ray 23. The irradiation part 58 further controls the therapeutic radioactive-ray irradiating device 16 so that the affected area is irradiated with the therapeutic radioactive ray 23. The irradiation part 58 further repeatedly performs the operations from shooting of the X-ray images to irradiation of the therapeutic radioactive ray 23 until the affected area of the patient 43 is irradiated with the dose of the therapeutic radioactive ray 23 indicated by the treatment plan.

Figure 4:
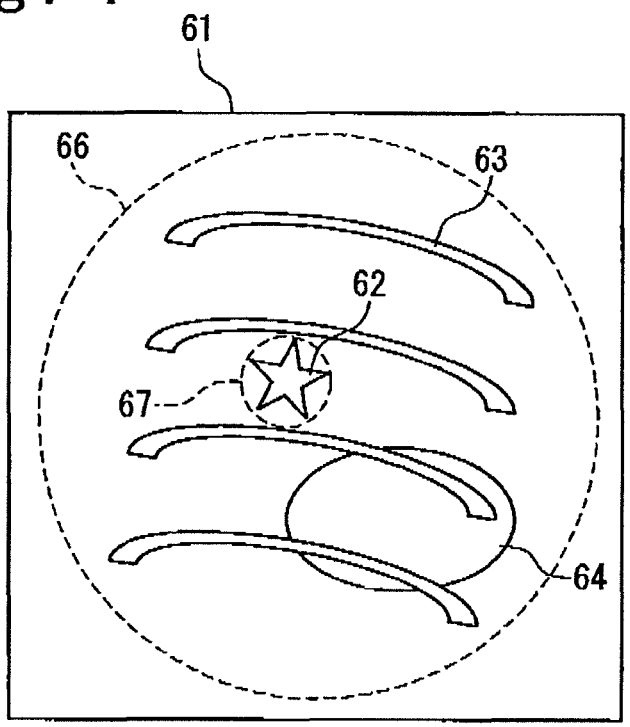
FIG. 4 is diagram of a DRR image.

FIG. 4 depicts the first DRR image generated by the matching data generation part 53. A first DRR image 61 includes a first region image 63, a second region image 62, and a third region image 64. The second region image 62 reflects an affected area of the patient 43. The first region image 63 reflects bones of the patient 43. Note that the bones can be larger than the affected area of the patient 43 and can be replaced by another region reflected on the X-ray image more clearly than the affected area of the patient 43. Such region is exemplified by a marker embedded inside the body of the patient 43. The third region image 64 reflects a risk organ of the patient 43. The risk organ is exemplified by a spinal cord.

The first DRR image 61 represents a first template area 66 and a second template area 67. The second template area 67 includes the second region image 62. The first template area 66 includes the first region image 63, and is larger than the second template area 67.

Figure 5:
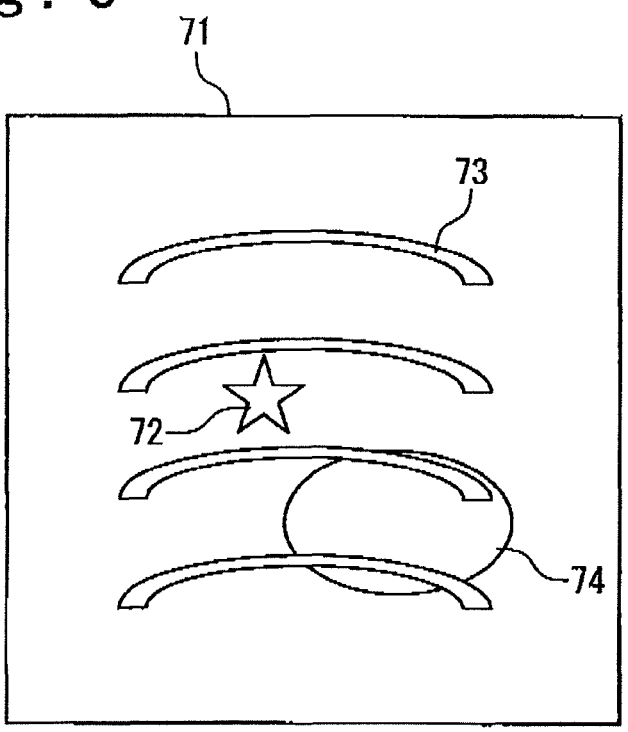
FIG. 5 is a diagram of an X-ray image.

FIG. 5 depicts a first X-ray image shot by the imager part 52. A first X-ray image 71 reflects a first region image 73, a second region image 72, and a third region image 74. The first region image 73 reflects bones of the patient 43. The second region image 72 reflects an affected area of the patient 43. The third region image 74 reflects a risk organ of the patient 43.

At this time, the first correction part 55 extracts from the first X-ray image 71 an area most similar to the first template area 66 to calculate a displacement amount. The displacement amount represents an x-direction displacement amount, a y-direction displacement amount, and a rotational displacement amount. The x-direction displacement amount represents a difference between x coordinates of a position where the first template area 66 of the first DRR image 61 is arranged and x coordinates of a position where the extracted area of the first X-ray image 71 is arranged. The y-direction displacement amount represents a difference between y coordinates of the position where the first template area 66 of the first DRR image 61 is arranged and y coordinates of the position where the extracted area of the first X-ray image 71 is arranged. The rotation displacement amount represents a difference between an orientation in which the first template area 66 of the first DRR image 61 is arranged and an orientation in which the retrieved area of the first X-ray image 71 is arranged. The first correction part 55 calculates a rotational correction amount and a translational correction amount based on the displacement amount.

At this time, the second correction part 56 extracts from the first X-ray image 71 an area most similar to the second template area 67 to calculate a displacement amount. The displacement amount represents an x-direction displacement amount, a y-direction displacement amount, and a rotational displacement amount. The x-direction displacement amount represents a difference between x coordinates of a position where the second template area 67 of the first DRR image 61 is arranged and x coordinates of a position where the extracted area of the first X-ray image 71 is arranged. The y-direction displacement amount represents a difference between y coordinates of the position where the second template area 67 of the first DRR image 61 is arranged and y coordinates of the position where the extracted area of the first X-ray image 71 is arranged. The rotation displacement amount represents a difference between an orientation in which the second template area 67 of the first DRR image 61 is arranged and an orientation in which the retrieved area of the first X-ray image 71 is arranged. The second correction part 56 calculates a translational correction amount based on the displacement amount.

At this time, since the second template area 67 is small compared with the first template area 66, the orientation of the area extracted based on the second template area 67 of the first X-ray image 71 has a large error compared with the orientation of the area extracted based on the second template area 67 of the first X-ray image 71. Therefore, the rotational correction amount calculated by the first correction part 55 is more accurate compared with the rotational correction amount calculated based on the orientation of the area extracted based on the second template area 67 of the first X-ray image 71.

It is known that the positional relation between the bones of the patient 43 and the affected area of the patient 43 is varied with time, and is not necessarily always constant. Therefore, the translational correction amount calculated by the second correction part 56 is more accurate compared with the translational correction amount calculated by the first correction part 55.

For this reason, the couch control part 57 can control the couch driving device 42 so that the affected area of the patient 43 is more accurately arranged at a predetermined position and orientation. As a result, the irradiation part 58 can control the swinging device 15 and the radioactive-ray irradiating device 16 so that the affected area of the patient 43 is more accurately irradiated with the therapeutic radioactive ray 23.

An embodiment of a radiotherapy apparatus control method according to the present invention is performed by the radiotherapy apparatus control apparatus 2, and includes an operation of adjusting the position of the patient and an operation of performing radiotherapy.

FIG. 6 depicts the operation of adjusting the position of the patient. A user first inputs, a previously-generated treatment plan to the radiotherapy apparatus control apparatus 2. The treatment plan represents three-dimensional data, and represents a combination of an irradiation angle and a dose. The three-dimensional data associates a plurality of transmittances with a plurality of voxels. The plurality of voxels correspond to a plurality of rectangular cuboids tightly filling a space where the patient 43 is arranged. The transmittance corresponding to each voxel represents an X-ray transmittance of a cube at a position corresponding to the voxel. The three-dimensional data represents stereoscopic shapes of a plurality of organs of the patient 43 laid on a bed and a plurality of positions where the plurality of organs are respectively arranged. The three-dimensional data further represents stereoscopic shapes of bones of the patient 43 laid on the bed and the positions of the bones, and represents a stereoscopic shape of an affected area of patent 43 and the position of the affected area. The irradiation angle represents a direction in which the affected area of the patient 43 is irradiated with the therapeutic radioactive ray 23, and represents a couch position, an O-ring rotation angle, and a gantry rotation angle. The couch position represents the position and orientation of the couch 41 with respect to the base. The O-ring rotation angle represents the position of the O ring 12 with respect to the base. The gantry rotation angle represents the position of the traveling gantry 14 with respect to the O ring 12. The dose represents a dose of the therapeutic radioactive ray 23 with which the patient 43 is irradiated at each irradiation angle.

The radiotherapy apparatus control apparatus 2 generates a first DRR image and a second DRR image based on the three-dimensional data. The first DRR image represents an image assumed to be generated by the first sensor array 32 when the couch 41 is arranged at the couch position, the O ring 12 is arranged at the O-ring rotation angle, and the traveling gantry 14 is arranged at the gantry rotation angle. The second DRR image, the first DRR image, represents an image assumed to be generated by the second sensor array 33 when the couch 41 is arranged at the couch position, the O ring 12 is arranged at the O-ring rotation angle, and the traveling gantry 14 is arranged at the gantry rotation angle.

The radiotherapy apparatus control apparatus 2 further calculates the first template area 66 and the second template area 67 reflected on the first DRR image based on the three-dimensional data and the first DRR image. The radiotherapy apparatus control apparatus 2 further calculates the first template area 66 and the second template area 67 reflected on the second DRR image based on the three-dimensional data and the second DRR image.

The user fixes the patient 43 to the couch 41 of the radiotherapy apparatus 3. The radiotherapy apparatus control apparatus 2 controls the couch driving device 42 so that the couch 41 is arranged at the couch position with respect to the base. The radiotherapy apparatus control apparatus 2 controls the rotary driving device 11 so that the O ring 12 is arranged at the O-ring rotation angle with respect to the base. The radiotherapy apparatus control apparatus 2 controls the traveling driving device of the radiotherapy apparatus 3 so that the traveling gantry 14 is arranged at the gantry rotation angle with respect to the O ring 12. The radiotherapy apparatus control apparatus 2 controls the first diagnostic X-ray source 24 so that a first X-ray image of the patient 43 is shot, and controls the first sensor array 32. The radiotherapy apparatus control apparatus 2 controls the second diagnostic X-ray source 25 so that a second X-ray image of the patient 43 is shot, and controls the second sensor array 33 (step S1).

By operating the input device, the user selects a first matching method from among a plurality of matching methods indicated by the radiotherapy apparatus control apparatus 2, and selects a second matching method from among the plurality of matching methods (step S2).

The radiotherapy apparatus control apparatus 2 corrects the first X-ray image to a gamma-corrected first X-ray image (step S3). The gamma-corrected first X-ray image is calculated so that a frequency distribution of a plurality of luminances represented by the gamma-corrected first X-ray image approximately coincides with a frequency distribution of a plurality of luminances represented by the first DRR image. That is, the first X-ray image is gamma-converted so that a gamma characteristic of the gamma-corrected first X-ray image coincides with a gamma characteristic of the first DRR image. The radiotherapy apparatus control apparatus 2 further corrects the second X-ray image to a gamma-corrected second X-ray image. The gamma-corrected second X-ray image is calculated so that a frequency distribution of a plurality of luminances represented by the gamma-corrected second X-ray image approximately coincides with a frequency distribution of a plurality of luminances represented by the second DRR image. That is, the second X-ray image is gamma-converted so that a gamma characteristic of the gamma-corrected second X-ray image coincides with a gamma characteristic of the second DRR image.

The radiotherapy apparatus control apparatus 2 further corrects the gamma-corrected first X-ray image to a luminance-range-corrected first X-ray image (step S4). The luminance-range-corrected first X-ray image is formed of pixels included within a predetermined luminance range among the plurality of pixels constructing the gamma-corrected first X-ray image. The luminance range represents a range of values that can be taken by the plurality of luminances respectively represented by the plurality of pixels constructing an image reflecting a first region (bones) on the first DRR image. The radiotherapy apparatus control apparatus 2 further corrects the gamma-corrected second X-ray image to a luminance-range-corrected second X-ray image. The luminance-range-corrected second X-ray image is formed of pixels included within a predetermined luminance range among the plurality of pixels constructing the gamma-corrected second X-ray image.

The radiotherapy apparatus control apparatus 2 further corrects the luminance-range-corrected first X-ray image to a gray-scale-roughness-corrected first X-ray image (step S5) The gray-scale-roughness-corrected first X-ray image is calculated so that the number of values (that is, the number of gray-scale levels) that can be taken by the plurality of luminances represented by the plurality of pixels constructing the gray-scale-roughness-corrected first X-ray image is smaller than the number of values (that is, the number of gray-scale levels) that can be taken by the plurality of luminances represented by the plurality of pixels constructing the luminance-range-corrected first X-ray image. The number of gray-scale levels of the gray-scale-roughness-corrected first X-ray image is calculated so that an image reflecting the first region (bones) can be sufficiently extracted from the gray-scale-roughness-corrected first X-ray image. The radiotherapy apparatus control apparatus 2 further corrects the luminance-range-corrected second X-ray image to a gray-scale-roughness-Corrected second X-ray image in a manner similar to that of the gray-scale-roughness-corrected first X-ray image.

The radiotherapy apparatus control apparatus 2 further uses the first matching method to extract an area most similar to the first template area 66 from the gray-scale-roughness-corrected first X-ray image and extract an area most similar to the first template area 66 from the gray-scale-roughness-corrected second X-ray image. The radiotherapy apparatus control apparatus 2 further calculates a rotational correction amount and a translational correction amount based on the position and orientation of the image of the first region reflected on the gray-scale-roughness-corrected first X-ray image, and further based on the position and orientation of the image of the first region reflected on the gray-scale-roughness-corrected second X-ray image (step S6).

The radiotherapy apparatus control apparatus 2 further corrects the gamma-corrected first X-ray image to a luminance-range-corrected first X-ray image (step S7). The luminance-range-corrected first X-ray image is formed of pixels included within a predetermined luminance range among the plurality of pixels constructing the gamma-corrected first X-ray image. The luminance range represents a range of values that can be taken by the plurality of luminances respectively represented by the plurality of pixels constructing an image reflecting a second region (affected area) on the first DRR image, and is smaller than a luminance range applied when a luminance-range-corrected first X-ray image is calculated by the first correction part 55. The radiotherapy apparatus control apparatus 2 further corrects the gamma-corrected second X-ray image to a luminance-range-corrected second X-ray image. The luminance-range-corrected second X-ray image is formed of pixels included within a predetermined luminance range among the plurality of pixels constructing the gamma-corrected second X-ray image.

The radiotherapy apparatus control apparatus 2 further corrects the luminance-range-corrected first X-ray image to a gray-scale-roughness-corrected first X-ray image (step S8). The gray-scale-roughness-corrected first X-ray image is calculated so that the number of values (that is, the number of gray-scale levels) that can be taken by the plurality of luminances represented by the plurality of pixels constructing the gray-scale-roughness-corrected first X-ray image is smaller than the number of values (that is, the number of gray-scale levels) that can be taken by the plurality of luminances represented by the plurality of pixels constructing the luminance range-corrected first X-ray image. The number of gray-scale levels of the gray-scale-roughness-corrected first X-ray image is calculated so that an image reflecting the second region (affected area) can be sufficiently extracted from the gray-scale-roughness-corrected first X-ray image. The radiotherapy apparatus control apparatus 2 further corrects the luminance-range-corrected second X-ray image to a gray-scale-roughness-corrected second X-ray image in a manner similar to that of the gray-scale-roughness-corrected first X-ray image.

The radiotherapy apparatus control apparatus 2 further uses a second matching method to extract an area most similar to the second template area 67 from the the gray-scale-roughness-corrected first X-ray image, and extracts an area most similar to the second template area 67 from the gray-scale-roughness-corrected second X-ray image. The radiotherapy apparatus control apparatus 2 further calculates a translational correction amount (step S9) based on the rotational correction amount calculated at step S6, further based on the position and orientation of the image of the second region reflected on the gray-scale-roughness-corrected first X-ray image, and still further based on the position and orientation of the image of the second region reflected on the gray-scale-roughness-corrected second X-ray image (step S9).

The radiotherapy apparatus control apparatus 2 controls the couch driving device 42 based on the rotational correction amount calculated at step S6 and the translational correction amount calculated at step S9. That is, after the couch 41 is rotated as indicated by the rotational correction amount calculated at step S6, the radiotherapy apparatus control apparatus 2 controls the couch driving device 42 so that the couch 41 is translated as indicated by the translational correction amount calculated at step S9 (step S10).

The radiotherapy operation is performed after the operation of adjusting the position of the patient. That is, after the couch 41, the O ring 12, and the traveling gantry 14 are arranged at the predetermined positions, the radiotherapy apparatus control apparatus 2 controls the first diagnostic X-ray source 24 and the first sensor array 32 so that a first tracking X-ray image of the patient 43 is shot, and controls the second diagnostic X-ray source 25 and the second sensor array 33 so that a second tracking X-ray image of the patient is shot.

The radiotherapy apparatus control apparatus 2 calculates the position and shape of the affected area of the patient 43 based on the first tracking X-ray image and the second tracking X-ray image. The radiotherapy apparatus control apparatus 2 controls the swinging device 15 so that the therapeutic radioactive irradiating device 16 is oriented to the calculated position. The radiotherapy apparatus control apparatus 2 controls the multi-leaf collimator 20 so that the shape of the affected area coincides with the irradiation field of the therapeutic radioactive ray 23. The radiotherapy apparatus control apparatus 2 further controls the therapeutic radioactive-ray irradiating device 16 so that the affected area is irradiated with a predetermined does of the therapeutic radioactive ray 23. The radiotherapy apparatus control apparatus 2 further periodically and repeatedly performs the operations from shooting of a tracking X-ray image to irradiation of the therapeutic radioactive ray 23 until the affected area of the patient 43 is irradiated with the dose of the therapeutic radioactive ray 23 indicated by the treatment plan. The period is exemplified by 0.2 seconds.

Since the first template area 66 is large compared with the second template area 67, the orientation of the area extracted based on the first template area 66 of the gray-scale-roughness-corrected first X-ray image has a small error compared with the orientation of the area extracted based on the second template area 67 of the gray-scale-roughness-corrected first X-ray image. Therefore, according to the radiotherapy apparatus control method as described above, the rotational correction amount calculated at step S6 is more accurate compared with the rotational correction amount calculated based on the orientation of the area extracted based on the second template area 67 of the gray-scale-roughness-corrected first X-ray image.

It is known that the positional relation between the patient 43 and the affected area of the patient 43 is varied with time, and is not necessarily always constant. Therefore, according to the radiotherapy apparatus control method as described above, the translational correction amount calculated at step S9 is more accurate compared with the translational correction amount calculated at step S6.

For this reason, according to the radiotherapy apparatus control method as described above, the radiotherapy apparatus control apparatus 2 can control the couch driving device 42 so that the affected area of the patient 43 is more accurately arranged at the predetermined position and orientation. As a result, the radiotherapy apparatus control apparatus 2 can control the swinging device 15 and the radioactive-ray irradiating device 16 so that the affected area of the patient 43 is more accurately irradiated with the therapeutic radioactive ray 23. According to the radiotherapy apparatus control method as described above, a set-up margin at the time of a treatment plan can be decreased.

Further, according to gamma conversion at step S3, even when the gamma characteristic of the device used when the three-dimensional data is generated indicated by the treatment plan is significantly different from the gamma characteristic of an imager of the radiotherapy apparatus 3, the first template area 66 and the second template area 67 can be more appropriately extracted from the X-ray image appropriately.

Still further, according to the setting of the luminance range at step S4, the amount of information when the first template area 66 is extracted from the X-ray image can be reduced. Still further, according to the setting of the luminance range at step S7, the amount of information when the second template area 67 is extracted from the X-ray image can be reduced. As a result, the radiotherapy apparatus control apparatus 2 can adjust the position of the patient 43 at higher speed.

Still further, according to the setting of the number of gray-scale levels at step S5, the amount of information when the first template area 66 is extracted from the X-ray image can be reduced. Still further, according to the setting of the number of gray-scale levels at step S8, the amount of information when the second template area 67 is extracted from the X-ray image can be reduced. As a result, the radiotherapy apparatus control apparatus 2 can adjust the position of the patient 43 at higher speed.

Note that the three-dimensional data indicated by the treatment plan can be generated by using the radiotherapy apparatus 3. At this time, the radiotherapy apparatus control apparatus 2 can more accurately adjust the position of the patient 43 in a manner similar to that of the embodiment described above. At this time, in the radiotherapy apparatus control apparatus 2, gamma conversion at step S3 can further be omitted. That is, a gamma-corrected i-th X-ray image (i=1, 2) can coincide with an i-th X-ray image.

Note that, in the radiotherapy apparatus control apparatus 2, the setting of a luminance range at steps S4 and S7 or the setting of the number of luminances at steps S5 and S8 can be omitted. That is, a luminance-range-corrected i-th X-ray image can coincide with the gamma-corrected i-th X-ray image, and the gray-scale-roughness-corrected i-th X-ray image can coincide with the luminance-range-corrected i-th X-ray image.

In another embodiment of the radiotherapy apparatus control apparatus according to the present invention, the matching method selection part 54 in the above-described embodiment is replaced by another matching method selection part. The matching method selection part adopts a feature point matching as a first matching method, and adopts a pattern matching as a second matching method. The feature point matching is a matching method suitable for matching of images with a large contrast. The pattern matching is a matching method suitable for matching of images with a small contrast. According to the radiotherapy apparatus control apparatus as described above, even when the first matching method and the second matching method are fixed, the position of the patient 43 can be more accurately adjusted in a manner similar to that of the radiotherapy apparatus control apparatus 2 in the above-described embodiment. Furthermore, when a matching method suitable for matching of both of the image of the first region and the image of the second region is present, the first matching method and the second matching method can coincide with the matching method.

In still another embodiment of the radiotherapy apparatus control apparatus according to the present invention, the imager part 52, the first correction part 55, and the second correction part 56 in the above-described embodiment are replaced by other imager part, first correction part, and second correction part.

The imager part further controls the traveling driving device of the radiotherapy apparatus 3 so that the traveling gantry 14 rotates about the rotation axis 18. The imager part further controls, when the traveling gantry 14 is rotated, the first diagnostic X-ray source 24 so that each first diagnostic X-ray 35 is emitted for exposure at a timing of arranging the first diagnostic X-ray source 24 at each predetermined plurality of shooting angles with respect to the O ring 12, and controls the second diagnostic X-ray source 25 so that each second diagnostic X-ray 36 is emitted for exposure at a timing of arranging the second diagnostic X-ray source 25 at each predetermined plurality of shooting angles with respect to the O ring 12. The imager part further controls the first sensor array 32 so that a first X-ray image is generated when the first diagnostic X-ray 35 is emitted for exposure, and controls the second sensor array 33 so that a second X-ray image is generated when the second diagnostic X-ray 36 is emitted for exposure. The imager part further creates three-dimensional data based on the plurality of first X-ray images and the plurality of the second X-ray images. The three-dimensional data associates a plurality of transmittances with a plurality of voxels in a manner similar to the three-dimensional data indicated by the treatment plan.

In a manner similar to that of the first correction part 55 in the above-described embodiment, the first correction part corrects the three-dimensional data generated by the image part to a gamma-corrected three-dimensional data, corrects the gamma-corrected three-dimensional data to a luminance-range-corrected three-dimensional data, and corrects the luminance-range-corrected three-dimensional data to a gray-scale-roughness-corrected three-dimensional data. The first correction part extracts from the gray-scale-roughness-corrected three-dimensional data a three-dimensional area most similar to the first template three-dimensional area reflecting bones of the patient 43 among the three-dimensional data indicated by the treatment plan, and calculates a rotational correction amount and a translational correction amount based on the position and orientation of the extracted three-dimensional area.

In a manner similar to that of the second correction part 56 in the above-described embodiment, the second correction part corrects the three-dimensional data generated by the imager part to a gamma-corrected three-dimensional data, corrects the gamma-corrected three-dimensional data to a luminance-range-corrected three-dimensional data, and corrects the luminance-range-corrected three-dimensional data to a gray-scale-roughness-corrected three-dimensional data. The second correction part extracts from the gray-scale-roughness-corrected three-dimensional data a three-dimensional area most similar to the second template three-dimensional area reflecting the affected region of the patient 43 among the three-dimensional data indicated by the treatment plan, and calculates a translation correction amount based on the position, and orientation of the extracted three-dimensional area and the rotational correction amount calculated by the first correction part.

The radiotherapy apparatus control apparatus as described above can accurately adjust the position of the patient 43 in a manner similar to that of the radiotherapy apparatus control apparatus 2 in the embodiment described above.

EXPLANATION OF THE REFERENCE NUMBERS IN THE DRAWINGS

1: RADIOTHERAPY SYSTEM
2: RADIOTHERAPY APPARATUS CONTROL APPARATUS
3; RADIOTHERAPY APPARATUS
11: ROTARY DRIVING DEVICE
12: O RING
14: TRAVELLING GANTRY
15: SWINGING DEVICE
16: THERAPEUTIC RADIOACTIVE-RAY IRRADIATING DEVICE
17; ROTATION AXIS
18: ROTATION AXIS
19: ISOCENTER
20: MULTI-LEAF COLLIMATOR
21: TILT AXIS
22: PAN AXIS
23: THERAPEUTIC RADIOACTIVE RAY
24: FIRST DIAGNOSTIC X-RAY SOURCE
25: SECOND DIAGNOSTIC X-RAY SOURCE
32: FIRST SENSOR ARRAY
33: SECOND SENSOR ARRAY
35: FIRST DIAGNOSTIC X-RAY
36: SECOND DIAGNOSTIC X-RAY
41: COUCH
42: COUCH DRIVING DEVICE
43: PATIENT
51: TREATMENT PLAN COLLECTION PART
52: IMAGER PART
53: MATCHING DATA GENERATION PART
54: MATCHING METHOD SELECTING PART
55: FIRST CORRECTION PART
56: SECOND CORRECTION PART
57: COUCH CONTROL PART
58: IRRADIATION PART
61: FIRST DRR IMAGE
62: SECOND REGION IMAGE
63: FIRST REGION IMAGE
64: THIRD REGION IMAGE
66: FIRST TEMPLATE AREA
67: SECOND TEMPLATE AREA
71: FIRST X-RAY IMAGE
72; SECOND. REGION IMAGE
73: FIRST REGION IMAGE
74; THIRD REGION IMAGE

The invention claimed is:

1. A radiotherapy apparatus control method comprising:
calculating a rotational correction amount and a first translational correction amount based on a position and orientation of a first region represented by a radioscopic image of a sample subject having the first region and a second region; and
calculating a second translational correction amount based on a position and orientation of the second region represented by the radioscopic: image and the rotational correction amount,
wherein the rotational correction amount and the first translational correction amount are calculated so that the first region is arranged at a predetermined region when a couch where the sample subject is arranged makes a rotational movement by the rotational correction amount and the couch is translated by the first translational correction amount,
the second translational correction amount is calculated so that the second region is arranged at a predetermined region when the couch where the sample subject is arranged makes a rotational movement by the rotational correction amount and the couch is translated by the second translational correction amount, and
the first region is larger than the second region.

2. The radiotherapy apparatus control method according to claim 1, further comprising:
collecting treatment plan three-dimensional data of the sample subject,
wherein the rotational correction amount and the first translational correction amount are calculated based on a first detection area matching a first template calculated based on the treatment plan three-dimensional data of the radioscopic image; and
the second translational correction amount is calculated based on a second detection area matching a second template calculated based on the treatment plan three-dimensional data of the radioscopic image and the rotational correction amount.

3. The radiotherapy apparatus control method according to claim 2, wherein the first detection area is calculated with a feature point matching, and
the second detection area is calculated with a pattern matching different from the feature point matching.

4. The radiotherapy apparatus control method according to claim 2, wherein the first detection area is calculated based on a first luminance-range-corrected radioscopic image converted from the radioscopic image,
a range that can be taken by a plurality of luminances represented by the first luminance-range-corrected radioscopic image is narrower than a range that can be taken by the plurality of luminances represented by the radioscopic image,
the second detection area is calculated based on a second luminance-range-corrected radioscopic image converted from the radioscopic image, and
a range that can be taken by a plurality of luminances represented by the second luminance-range-corrected radioscopic image is narrower than the range that can be taken by the plurality of luminances represented by the radioscopic image.

5. The radiotherapy apparatus control method according to claim 2, wherein the first detection area is calculated based on a gray-scale-roughness-corrected radioscopic image converted from the radioscopic image, and a gray scale of the radioscopic image is finer than a gray scale of the gray-scale-roughness-corrected radioscopic image.

6. The radiotherapy apparatus control method according to claim 2, wherein the first detection area is calculated based on the gray-scale-corrected radioscopic image converted from the radioscopic image so that a frequency distribution of a plurality of luminances represented by the gray-scale-corrected radioscopic image approximately coincides with a frequency distribution of a plurality of luminances represented by a DRR image calculated from the treatment plan three-dimensional data, and the second detection area is calculated based on the gray-scale-corrected radioscopic image.

7. A radiotherapy apparatus control apparatus comprising:

an imager part that shoots a radioscopic image of a sample subject having a first region and a second region;

a first correction part that calculates a rotational correction amount and a first translational correction amount based on a position and orientation of the first region represented by the radioscopic image;

a second correction part that calculates a rotational correction amount and a second translational correction amount based on a position and orientation of the second region represented by the radioscopic image; and a couch control part that controls a couch driving device that drives the couch so that the couch where the sample subject is arranged rotationally moves by the rotational correction amount and the couch is translated by the second translational correction amount, wherein the first region is larger than the second region.

8. The radiotherapy apparatus control apparatus according to claim 7, further comprising:

a treatment plan collection part that collects treatment plan three-dimensional data of the sample subject, wherein the first correction part is configured to calculate the rotational correction amount and the first translational correction amount based on a first detection area matching a first template calculated based on the treatment plan three-dimensional data of the radioscopic image, and the second correction part is configured to calculate the second translational correction amount based on a second detection area matching a second template calculated based on the treatment plan three-dimensional data of the radioscopic image and the rotational correction amount.

9. The radiotherapy apparatus control apparatus according to claim 8, wherein the first correction part calculates the first detection area with a feature point matching, and the second correction part calculates the second detection area with a pattern matching different from the feature point matching.

10. The radiotherapy apparatus control apparatus according to claim 8, wherein the first correction part is configured to calculate the first detection area based on a first luminance-range-corrected radioscopic image converted from the radioscopic image, the range that can be taken by a plurality of luminance represented by the first luminance-range-corrected radioscopic image is narrower than a range that can be taken by the plurality of luminances represented by the radioscopic image, the second correction part is configured to calculate the second detection area based on a second luminance-range-corrected radioscopic image converted from the radioscopic image, and a range that can be taken by a plurality of luminances represented by the second luminance-range-corrected radioscopic image is narrower than the range that can be taken by the plurality of luminances represented by the radioscopic image.

11. The radiotherapy apparatus control apparatus according to claim 8, wherein the first correction part is configured to calculate the first detection area based on a gray-scale-roughness-corrected radioscopic image converted from the radioscopic image, and a gray scale of the radioscopic image is finer than a gray scale of the gray-scale-roughness-corrected radioscopic image.

12. The radiotherapy apparatus control apparatus according to claim 8, wherein the first correction part is configured to calculate the first detection area based on the gray-scale-corrected radioscopic image converted from the radioscopic image so that a frequency distribution of a plurality of luminances represented by the gray-scale-corrected radioscopic image approximately coincides with a frequency distribution of a plurality of luminances represented by a DRR image calculated from the treatment plan three-dimensional data, and the second correction part is configured to calculate the second detection area based on the gray-scale-corrected radioscopic image.

13. The radiotherapy apparatus control apparatus according to claim 7, further comprising:

an irradiation part configured to control the therapeutic radioactive-ray irradiating device so that the therapeutic radioactive ray is emitted for exposure onto the second region.

14. The radiotherapy apparatus control apparatus according to claim 13, wherein the irradiation part is configured to control, based on the other radioscopic image, a swing device that drives a treatment radioactive-ray irradiating device so that, after the imager that shots the radioscopic image is used to shoot another radioscopic image of the sample subject, the treatment radioactive ray is emitted for exposure onto the second region.

* * * * *